US012588924B2

(12) United States Patent
del Nido et al.

(10) Patent No.: US 12,588,924 B2
(45) Date of Patent: Mar. 31, 2026

(54) MINIMALLY INVASIVE DISSECTOR FOR INTER-LAYER PROCEDURES

(71) Applicant: Children's Medical Center Corporation, Boston, MA (US)

(72) Inventors: Pedro Jose del Nido, Lexington, MA (US); Borami Shin Lee, Dorchester, MA (US); Christopher James Payne, Cambridge, MA (US); Mossab Ym Saeed, Revere, MA (US)

(73) Assignee: The Children's Medical Center Corporation, Boston, MA (US)

( * ) Notice: Subject to any disclaimer, the term of this patent is extended or adjusted under 35 U.S.C. 154(b) by 726 days.

(21) Appl. No.: 17/898,892

(22) Filed: Aug. 30, 2022

(65) Prior Publication Data

US 2023/0000516 A1 Jan. 5, 2023

Related U.S. Application Data

(63) Continuation of application No. PCT/US2021/021684, filed on Mar. 10, 2021.

(Continued)

(51) Int. Cl.
*A61B 17/32* (2006.01)
*A61B 1/00* (2006.01)
(Continued)

(52) U.S. Cl.
CPC .. *A61B 17/320016* (2013.01); *A61B 1/00087* (2013.01); *A61B 1/05* (2013.01); *A61B 1/313* (2013.01); *A61B 2017/320044* (2013.01)

(58) Field of Classification Search
CPC ......... A61B 1/00087; A61B 1/32; A61B 1/05; A61B 1/313; A61B 17/320016; A61B 2017/320044; A61B 2017/2926
(Continued)

(56) References Cited

U.S. PATENT DOCUMENTS 5,439,478 A * 8/1995 Palmer ............... A61B 1/00087
606/205
5,569,299 A * 10/1996 Dill ........................ A61B 10/06
606/208
(Continued)

FOREIGN PATENT DOCUMENTS

CA        2310426        5/1999
CA        2314785        4/2007
WO    WO-2021183632        9/2021

OTHER PUBLICATIONS

EPO, "EP Application No. 21767189.0 Extended Search Report mailed Feb. 12, 2024", 5 pages.
(Continued)

*Primary Examiner* — Anh Tuan T Nguyen
*Assistant Examiner* — Li-Ting Song
(74) *Attorney, Agent, or Firm* — Strategic Patents, P.C.

(57) ABSTRACT

A device for minimally invasive, inter-layer surgical procedures advantageously forms a wedge for advancing between adjacent tissue layers and provides a jaw that can be actuated to create a working space for a cutting tool and other instruments within a plane between the tissue layers. The device may also usefully employ an open or wireframe structure for the opposing jaws to preventing tissue or fluid accumulation between the jaws and maximize visibility around the surgical site.

20 Claims, 8 Drawing Sheets

Related U.S. Application Data

(60) Provisional application No. 62/987,495, filed on Mar. 10, 2020.

(51) Int. Cl.
*A61B 1/05* (2006.01)
*A61B 1/313* (2006.01)

(58) Field of Classification Search
USPC ........................................................ 600/198
See application file for complete search history.

(56) References Cited

U.S. PATENT DOCUMENTS

| | | | |
|---|---|---|---|
| 5,591,183 A | 1/1997 | Chin | |
| 5,626,609 A * | 5/1997 | Zvenyatsky | A61B 17/29 |
| | | | 606/208 |
| 5,667,473 A | 9/1997 | Finn et al. | |
| 5,667,480 A | 9/1997 | Knight et al. | |
| 5,667,526 A * | 9/1997 | Levin | A61B 17/29 |
| | | | 606/205 |
| 5,860,997 A | 1/1999 | Bonutti | |
| 5,902,315 A | 5/1999 | Dubois | |
| 5,913,870 A | 6/1999 | Defonzo et al. | |
| 5,984,938 A | 11/1999 | Yoon | |
| 6,036,713 A | 3/2000 | Kieturakis | |
| 6,053,933 A | 4/2000 | Balazs et al. | |
| 6,099,550 A | 8/2000 | Yoon | |
| 6,387,043 B1 | 5/2002 | Yoon | |
| 6,419,626 B1 | 7/2002 | Yoon | |
| 6,596,010 B1 | 7/2003 | Hermann et al. | |
| 6,743,239 B1 * | 6/2004 | Kuehn | A61B 17/1285 |
| | | | 600/101 |
| 7,981,133 B2 | 7/2011 | Chin | |
| 8,216,154 B2 | 7/2012 | Freeman et al. | |
| D675,319 S | 1/2013 | Huertgen et al. | |
| 8,343,035 B2 | 1/2013 | To | |
| 8,721,527 B2 | 5/2014 | Braam et al. | |
| 8,803,960 B2 | 8/2014 | Sonnenschein et al. | |
| 8,834,358 B2 | 9/2014 | Mckinley et al. | |
| 8,852,088 B2 * | 10/2014 | Ransden | A61B 17/0281 |
| | | | 606/205 |
| 9,662,133 B2 | 5/2017 | Feuer et al. | |
| 9,717,399 B2 | 8/2017 | Newman | |
| 9,918,708 B2 | 3/2018 | Livne et al. | |
| 10,085,733 B2 | 10/2018 | Diao et al. | |
| 10,085,833 B2 | 10/2018 | Piers et al. | |
| 2003/0065349 A1 | 4/2003 | Hess et al. | |
| 2004/0059191 A1 * | 3/2004 | Krupa | A61M 25/0136 |
| | | | 600/146 |
| 2004/0102804 A1 | 5/2004 | Chin | |
| 2004/0193211 A1 | 9/2004 | Voegele et al. | |
| 2007/0060794 A1 | 3/2007 | Efinger et al. | |
| 2008/0058590 A1 | 3/2008 | Saadat et al. | |
| 2008/0154297 A1 | 6/2008 | Lee et al. | |
| 2008/0249556 A1 | 10/2008 | Yamatani | |
| 2010/0168610 A1 | 7/2010 | Lacombe et al. | |
| 2010/0292532 A1 | 11/2010 | Kadykowski et al. | |
| 2010/0292533 A1 | 11/2010 | Kasahara et al. | |
| 2011/0106079 A1 * | 5/2011 | Garrison | A61B 18/1445 |
| | | | 606/52 |
| 2013/0178865 A1 | 7/2013 | Singh et al. | |
| 2014/0320621 A1 | 10/2014 | Sonnenschein et al. | |
| 2014/0323800 A1 | 10/2014 | Dye | |
| 2014/0357946 A1 | 12/2014 | Golden et al. | |
| 2015/0073216 A1 | 3/2015 | Papay | |
| 2015/0366440 A1 | 12/2015 | Rothe et al. | |
| 2016/0038133 A1 * | 2/2016 | Smith | A61B 17/320016 |
| | | | 600/204 |
| 2016/0367311 A1 * | 12/2016 | Gerrans | A61B 10/02 |
| 2017/0056038 A1 * | 3/2017 | Hess | A61B 17/295 |
| 2017/0112523 A1 | 4/2017 | Jagelski et al. | |
| 2017/0296212 A1 | 10/2017 | Ding et al. | |
| 2018/0064487 A1 * | 3/2018 | Krastins | A61B 18/1485 |
| 2019/0000481 A1 | 1/2019 | Harris et al. | |
| 2019/0008603 A1 * | 1/2019 | Hansen | A61B 17/062 |
| 2019/0150725 A1 | 5/2019 | Ramanujam et al. | |
| 2019/0150968 A1 | 5/2019 | Winstanley et al. | |
| 2020/0375620 A1 * | 12/2020 | Demmy | A61B 17/32 |
| 2021/0386428 A1 * | 12/2021 | Larsen | A61B 17/122 |

OTHER PUBLICATIONS

WIPO, "PCT Application No. PCT/US21/21684 International Preliminary Report on Patentability mailed Sep. 22, 2022", 13 pages.

ISA/US, "PCT Application No. PCT/US21/21684 International Search Report and Written Opinion mailed May 27, 2021", 20 pages.

* cited by examiner

MINIMALLY INVASIVE DISSECTOR FOR INTER-LAYER PROCEDURES

CROSS-REFERENCE TO RELATED APPLICATIONS

This application is a bypass continuation that claims priority to International Patent Application No. PCT/US21/21684 filed on Mar. 10, 2021, which claims priority to U.S. Provisional Patent Application No. 62/987,495 filed on Mar. 10, 2020, where the entire content of each of the foregoing is incorporated herein by reference.

GOVERNMENT LICENSE RIGHTS

This invention was made with government support under Grant Number HL132655, awarded by the National Institutes of Health. The Government has certain rights in the invention.

TECHNICAL FIELD

The present disclosure generally relates to minimally invasive surgical instruments, and more specifically to minimally invasive surgical instruments for dissection between tissue layers.

BACKGROUND

While there has been considerable development in minimally invasive surgical instruments for operating in spatial cavities, less attention has been given to the design of instruments for operating within layers of tissue. Some devices such as mediastinoscopes are generally configured to create a working space within naturally occurring cavities; however, there remains a need for improved devices, systems, and methods for performing minimally invasive surgical procedures between tissue layers, particularly where adhesions or other tissue conjoins adjacent layers.

SUMMARY

A device for minimally invasive, inter-layer surgical procedures advantageously forms a wedge for advancing between adjacent tissue layers and provides a jaw that can be actuated to create a working space for a cutting tool and other instruments within a plane between the tissue layers. The device may also usefully employ an open or wireframe structure for the opposing jaws to preventing tissue or fluid accumulation between the jaws and to maximize visibility around the surgical site.

In one aspect, an endoscopic device disclosed herein may include: a tube having a distal end region, a proximal end region, and a central axis passing through the distal end region, the tube defining a channel from the proximal end region to the distal end region; a first jaw extending from the distal end region of the endoscopic device on a first side of a plane through the central axis, the first jaw having a first interior surface oriented toward the central axis and a first exterior surface oriented away from the central axis, the first jaw defining a first opening passing through the first jaw from the first interior surface to the first exterior surface; a second jaw extending from the distal end region of the endoscopic device, the second jaw pivotally coupled to the distal end region by a pivot on a second side of the plane opposing the first side, the second jaw including a second interior surface facing the first jaw and a second exterior surface facing away from the first jaw, the second jaw defining a second opening passing through the second jaw from the second interior surface to the second exterior surface, the second jaw having a closed position in which the first jaw and the second jaw are bounded by a wedge formed by two planar surfaces intersecting at a vertex on the first side of the plane, and the second jaw movable about the pivot to an open position where a second distal end of the second jaw moves across central axis to the second side of the plane to create a working volume about the plane between a first distal end of the first jaw and the second distal end of the second jaw; and an actuator operable to move the second jaw between the closed position and the open position.

Implementations may include one or more of the following features. The endoscopic device may further include a camera having a field of view directed toward the working volume between the first distal end of the first jaw and the second distal end of the second jaw. The wedge may contact a cross section of the first exterior surface of the first jaw and the second exterior surface of the second jaw in a second plane orthogonal to the plane through the central axis, where the wedge forms an angle of about five degrees to about thirty degrees. The wedge may form an envelope about the first exterior surface of the first jaw and the second exterior surface of the second jaw having an angle of about five to about sixty degrees. The wedge may be an asymmetrical wedge. A first planar surface of the wedge may extend from and be parallel to an exterior side of the tube. The vertex of the wedge may be radially closer to an exterior of the tube than the central axis of the tube. The wedge may include a first planar surface substantially parallel to the central axis and aligned with a point on an exterior surface of the distal end region of the tube, and a second planar surface intersecting a radially opposing point on the exterior surface of the distal end region of the tube. The first planar surface and the second planar surface may form an interior angle of the wedge of about ten to thirty degrees. The first exterior surface of the first jaw may extend from and be aligned with an exterior surface of the distal end region of the tube. The first jaw may be a wireframe structure formed about the first opening such that the first opening spans a majority of a surface area of the first exterior surface. The second jaw may be a wireframe structure formed about the second opening such that the second opening spans a majority of a surface area of the second exterior surface. The endoscopic device may further include a handle on the proximal end region of the tube, the handle coupled to the second jaw through a jaw transmission configured to rotate the second jaw about the pivot in response to a movement of the handle. The endoscopic device may further include a sheet metal linkage for communicating a force from the handle to the distal end region for rotation of the second jaw about the pivot. The endoscopic device may further include a gear and capstan for communicating a force from the handle to the distal end region for rotation of the second jaw about the pivot. The endoscopic device may further include serrations on the first exterior surface of the first jaw oriented to resist a retreat of the endoscopic device along a forward surgical path. The endoscopic device may further include serrations on the second exterior surface of the second jaw oriented to resist a retreat of the endoscopic device along a forward surgical path.

In one aspect, an endoscopic device disclosed herein may include: a first jaw fixed to and extending from a distal end region of the endoscopic device on a first side of a plane through an axis of the endoscopic device; a second jaw extending from the distal end region of the endoscopic device, the second jaw pivotally coupled to the distal end region by a pivot on a second side of the plane opposing the first side, the first jaw and the second jaw having a closed position bounded by an asymmetrical wedge, the second jaw movable about the pivot to an open position where a second distal end of the second jaw moves across central axis to the second side of the plane to create a working volume between the first jaw and the second jaw; and an actuator operable to move the second jaw between the closed position and the open position.

Implementations may include one or more of the following features. The first jaw may include a first interior surface oriented toward the central axis and a first exterior surface oriented away from the central axis, the first jaw defining a first opening passing through the first jaw from the first interior surface to the first exterior surface. The second jaw may include a second interior surface facing the first jaw and a second exterior surface facing away from the first jaw, the second jaw defining a second opening passing through the second jaw from the second interior surface to the second exterior surface.

BRIEF DESCRIPTION OF THE DRAWINGS

The foregoing and other objects, features, and advantages of the devices, systems, and methods described herein will be apparent from the following description of particular embodiments thereof, as illustrated in the accompanying drawings. The drawings are not necessarily to scale, emphasis instead being placed upon illustrating the principles of the devices, systems, and methods described herein.

DETAILED DESCRIPTION

Embodiments will now be described more fully hereinafter with reference to the accompanying figures, in which preferred embodiments are shown. All documents mentioned herein are hereby incorporated by reference in their entirety. References to items in the singular should be understood to include items in the plural, and vice versa, unless explicitly stated otherwise or clear from the context. Grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth.

Recitation of ranges of values herein are not intended to be limiting, referring instead individually to any and all values falling within the range unless otherwise indicated, and each separate value within such a range is incorporated into the specification as if it were individually recited herein. The words "about," "approximately," or the like, when accompanying a numerical value, are to be construed as indicating a deviation as would be appreciated by one of ordinary skill in the art to operate satisfactorily for an intended or stated purpose. Ranges of values and/or numeric values are provided herein as examples only, and do not constitute a limitation on the scope of the described embodiments. The use of examples or exemplary language ("e.g.," "such as," or the like) is intended merely to better illuminate the embodiments and does not pose a limitation on the scope of the disclosed embodiments or the claims. No language in the specification should be construed as indicating any unclaimed element as essential to the practice of the embodiments.

In the following description, terms such as "first," "second," "top," "bottom," "up," "down," "backward," "forward," and the like, are words of convenience and are not to be construed as limiting terms unless specifically stated to the contrary.

Described herein are devices, systems, and methods related to various surgical instruments and their applications in minimally invasive surgeries involving interlayer tissue dissection. However, a person of ordinary skill in the art will recognize that other applications are possible and that applications of the systems and methods described herein are not limited to those explicitly described in this disclosure. For example, the devices, systems, and methods described herein may be used in other surgeries, particularly for surgeries involving the creation of working space between joined or otherwise adjacent layers of tissue.

Figure 1:
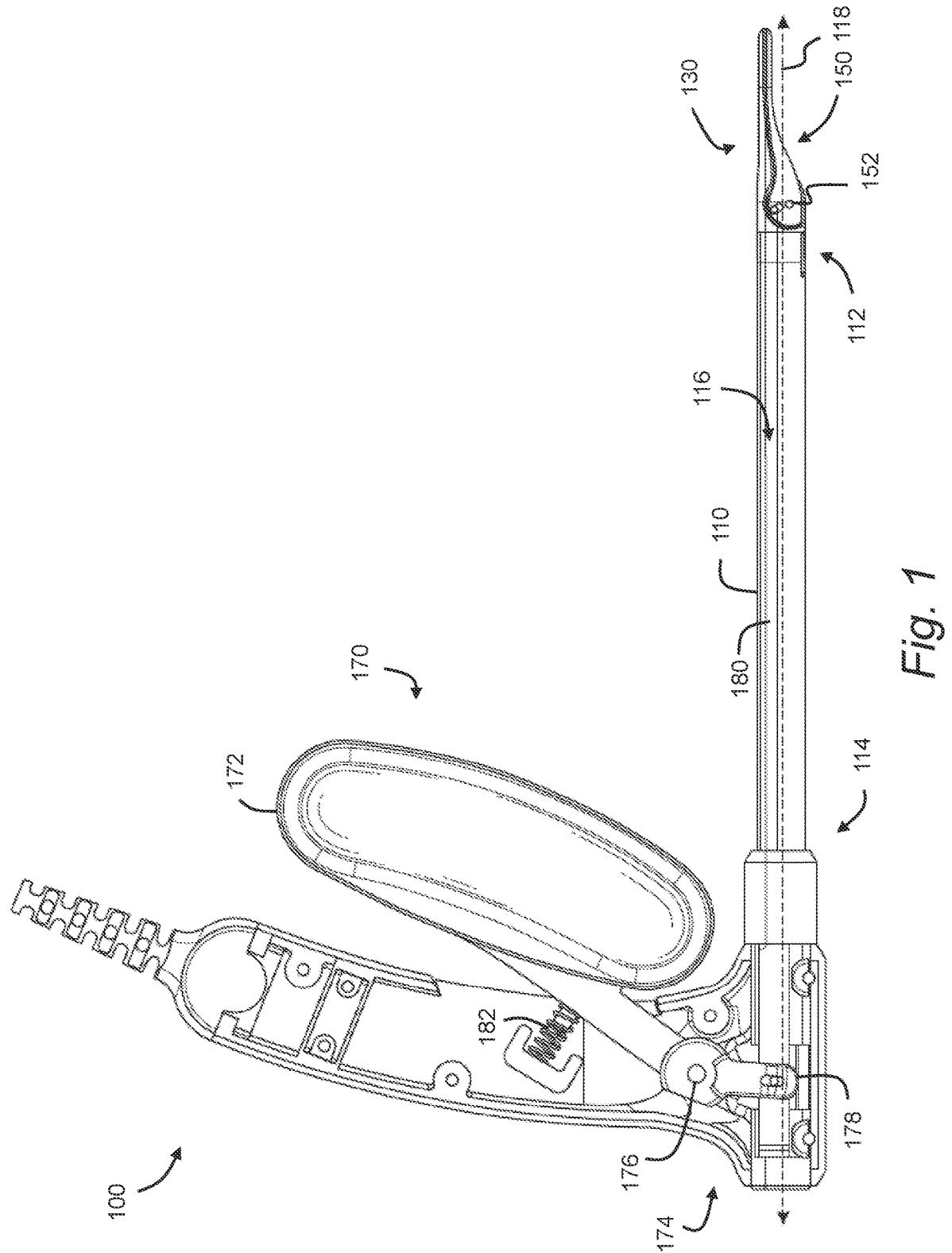
FIG. 1 shows a cross-section of an endoscopic device with a jaw in a closed position.

FIG. 1 shows a cross-section of an endoscopic device with a jaw in a closed position. In general, the endoscopic device 100 may include a tube 110, a first jaw 130, a second jaw 150, and an actuator 170.

The tube 110 may have any circular, elliptical, or other cross-sectional shape, and may generally have an exterior surface with a finish suitable for use in surgical procedures. The tube may be formed, for example, from any biocompatible plastic, surgical stainless steel, or other suitable materials. The tube 110 may include a distal end region 112 to be deployed to a surgical site during use, and a proximal end region 114 from which a surgeon or other operator can control the endoscopic device 100 during a procedure. The tube 110 may define a channel 116 from the proximal end region 114 to the distal end region 112, e.g., for coupling controls on the proximal end region 114 to components on the distal end region 112, for coupling electronics on the proximal end region 114 to a camera or other active components positioned at the distal end region 112, for deploying other surgical tools and the like to a surgical site, and so forth. The tube 110 may also generally include a central axis 118 passing through and extending from the distal end region 112.

The first jaw 130 may be, e.g., a fixed jaw or the like extending from the distal end region of the endoscopic device. The second jaw 150 may be pivotally coupled to the distal end region by a pivot 152 and may be controllably rotated by an actuator to extend away from the first jaw 130. As an advantage, a fixed jaw simplifies mechanical design of the endoscopic device 100, and can provide a strong, fixed contact surface that is able to support consistent, forward movement of the endoscopic device 100 during a procedure.

However, it will be understood that the first jaw 130 may also be a movable jaw that can pivot or otherwise move to displace tissue and create a working volume for a dissection or other procedure.

An actuator 170 may be positioned at the proximal end region 114 of the endoscopic device 100 and may be operable to move the second jaw 150 between a closed position and an open position, e.g., by rotating the second jaw 150 about the pivot 152. In general, the actuator 170 may include a handle 172 or other user-operable control coupled to the second jaw 150 through a jaw transmission 174 configured to rotate the second jaw 150 about the pivot 152 in response to a movement of the handle 172. The jaw transmission 174 may, for example, include a second pivot 176 and an arm 178 that couple the handle 172 to a linkage 180 such as a sheet metal linkage that translates movement of the handle 172 into a linear movement along (or parallel to) the central axis 118 of the tube 110 in order to communicate a force from the handle 172 to the distal end region 112 for rotation of the second jaw 150 about the pivot 152. The jaw transmission 174 may also include a spring 182 or other mechanism that biases the actuator 170 so that the second jaw 150 is in a closed position in the absence of external forces, e.g., in the absence of a user activation of the handle 172. In FIG. 1, this bias includes a clockwise bias of the handle 172 about the second pivot 176 so that the linkage 180 is biased to the left and the second jaw 150 is responsively biased in a counter-clockwise or closed position. It will be understood that other configurations are possible for the actuator 170, for example by positioning the handle 172 on the opposite side of the actuator 170 and configuring the jaw transmission 174 to open the second jaw 150 in response to a clockwise movement (in FIG. 1) of the handle 172.

Figure 2:
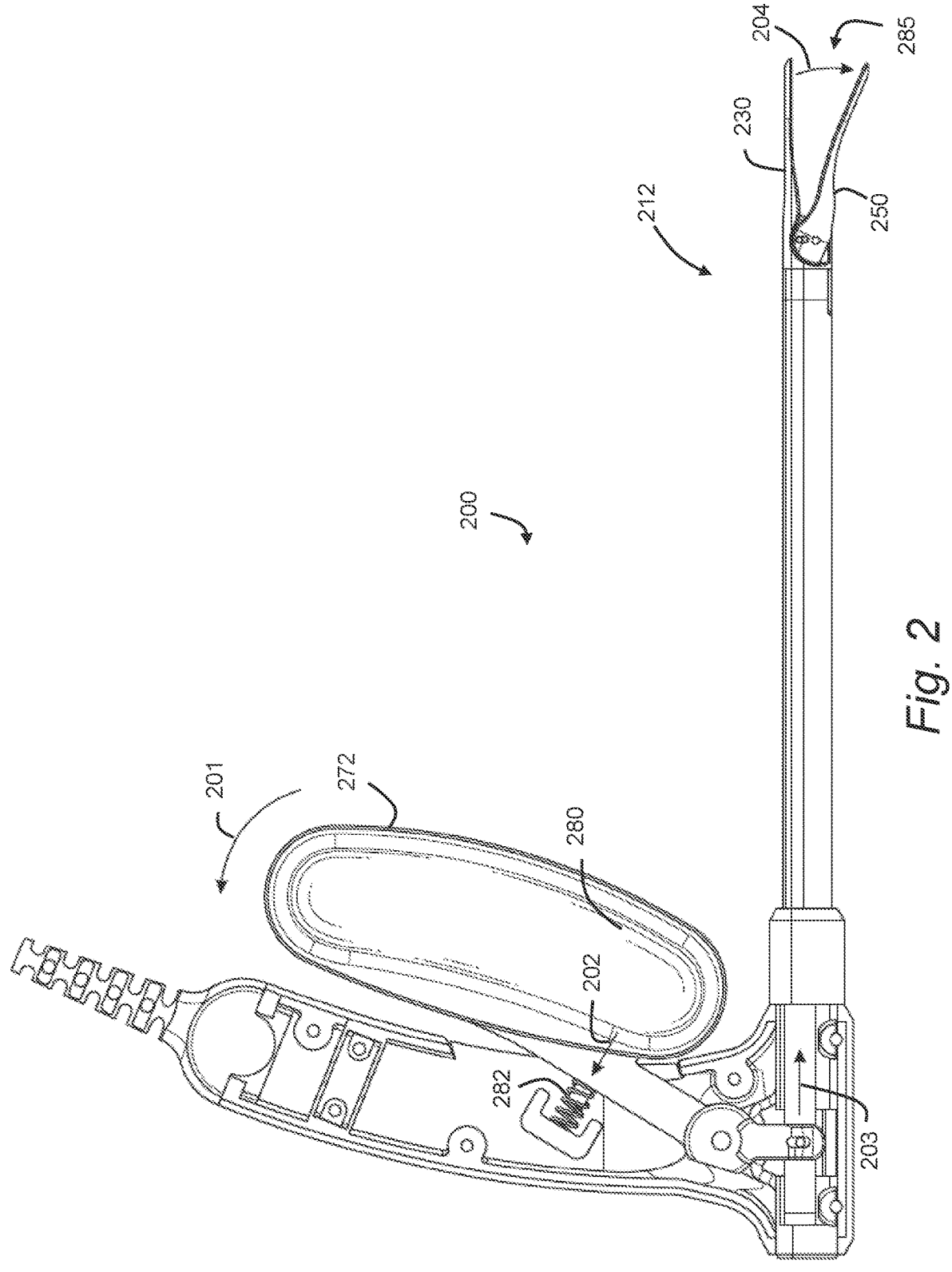
FIG. 2 shows a cross-section of an endoscopic device with a jaw in an open position.

FIG. 2 shows a cross-section of an endoscopic device with a jaw in an open position. In general, the endoscopic device 200 may be any of the endoscopic devices described herein, except as specifically noted otherwise. As illustrated, a handle 272 may be rotated counterclockwise against a bias of a spring 282. In response to this rotation, a force may be applied to move a linkage 280 toward a distal end region 212 of the endoscopic device 200, causing a second jaw 250 to rotate clockwise about a pivot 252 into an open position where a second jaw 250 is separated from a first jaw 230 to create a working space 285 therebetween. It will be noted that the illustrated embodiment includes a fixed jaw (the first jaw 230) and a moving jaw (the second jaw 250). While this is not strictly required for a working dissection device, this approach advantageously reduces the number of moving parts and failure points in the design, while permitting the limited cross-section and volume of an endoscopic device to be focused on the mechanically integrity and strength of a single, moving jaw. This is also well adapted to use in certain clinical applications, such as to prepare for a resternotomy, where the fixed jaw can rest against a relatively rigid structure such as the sternum and the moving jaw can displace relatively soft tissue and structures adjacent to the sternum.

The coupling of the handle 272 to the second jaw 250 is generally illustrated by a series of arrows (201, 202, 203, 204) showing a direction of movement of the handle 272, the spring 282, the linkage 280, and the second jaw 250, respectively.

Figures 3, 4:
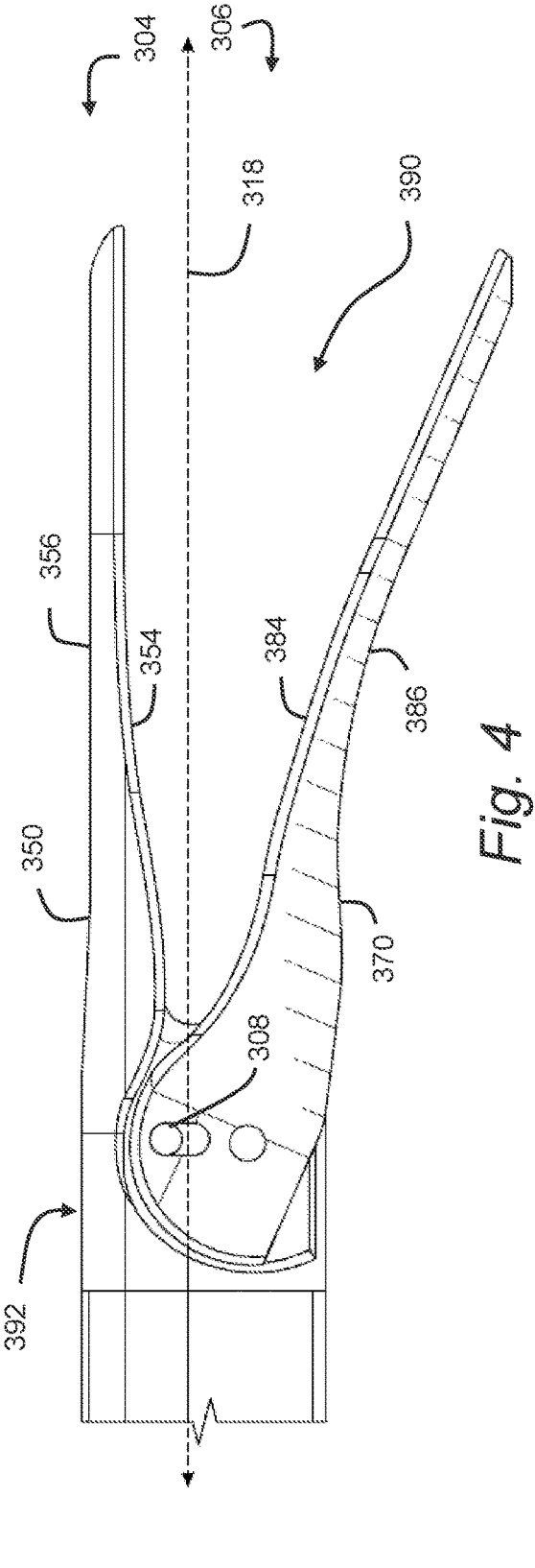
FIG. 3 shows a cross-section of an endoscopic device with a jaw in a closed position.
FIG. 4 shows a cross-section of an endoscopic device with a jaw in an open position.

FIG. 3 shows a cross-section of an endoscopic device with a jaw in a closed position. The endoscopic device 300 may be any of the endoscopic devices described herein, except as specifically noted otherwise. In general, the endoscopic device 300 may include a first jaw 350 and a second jaw 370 extending from a distal end region 312 of the endoscopic device 300. In a closed position, as illustrated, a first distal end 394 of the first jaw 350 may approach or contact a second distal end 396 of the second jaw 370. In this context, it will be understood that the first distal end 394 and the second distal end 396 identify general regions toward the ends of the corresponding jaws 350, 370 rather than specific points, unless otherwise indicated to the contrary.

The first jaw 350, which may be a fixed jaw that remains stationary relative to a tube 310 of the endoscopic device 300, may extend from the distal end region 312 on a first side 304 of a plane through a central axis 318 passing through and extending from the distal end region 312 of the tube 310. Although the plane is not shown, it will be understood that the plane extends orthogonally to the plane of FIG. 3 and intersects the central axis 318, dividing the cross sectional view into areas on the first side 304 of the plane (on the top of the figure) and a second side 306 of the plane (on the bottom of the figure). It will also be understood that while the axis is referred to as a "central" axis, this does not imply that the axis is precisely geometrically centered within the tube 310 of the endoscopic device. Rather this language is intended to indicate that the central axis 318 lies within an exterior surface of the tube 310 around the distal end region 312 of the endoscopic body, as generally illustrated in FIG. 3.

The second jaw 370, which may be a movable jaw that is controllable from a handle at a proximal end of the endoscopic device 300, may extend from the distal end region 312 of the endoscopic device 300, and contact or nearly contact the first jaw 350 when in a closed position as shown in FIG. 3. The second jaw 370 may be pivotally coupled to the distal end region by a pivot 352 on the second side 306 of the plane opposing the first side 304. This arrangement advantageously facilitates a rotation of the second jaw 370 that creates a working volume located between the jaws and generally aligned with an exit of the tube 310 for access by surgical devices, cameras, and so forth.

FIG. 4 shows a cross-section of an endoscopic device with a jaw in an open position. The endoscopic device 400 may be any of the endoscopic devices described herein, except as specifically noted otherwise. In general, a forward movement (left to right in the figure) by a pin 308 coupled to a linkage may cause a rotation of the second jaw 370 into an open position to create a working volume 390 between the first jaw 350 and the second jaw 370 along the central axis 318 where a dissection tool or the like can be deployed through the tube 310 and manipulated in a surgical procedure, e.g., to sever connective tissue between two adjacent tissue layers and facilitate advancement of the endoscopic device 300. In general, the first jaw 350 may have a first interior surface 354 oriented toward the central axis 318 and a first exterior surface 356 oriented away from the central axis 318. In one aspect, the first exterior surface 356 of the first jaw 350 may extend from and be aligned with an exterior surface 392 of the distal end region 312 of the tube 310 of the endoscopic device 300. The first exterior surface 356 may also or instead be shaped to follow a layer of tissue along a bone, organ, or other surface when advanced into a surgical site, and/or to urge adjacent layers of tissue apart to assist with dissection.

Similarly, the second jaw 370 may have a second interior surface 384 facing the first jaw 350 and a second exterior surface facing away from the first jaw 350. In general, the second jaw 370 may be movable about the pivot 352 to an open position (as illustrated) wherein the second distal end 396 of the second jaw 370 moves across the central axis 318 to the second side 306 of the plane to create the working volume 390 about the plane between the first distal end 394 of the first jaw 350 and the second distal end 396 of the second jaw 370.

Figure 5:
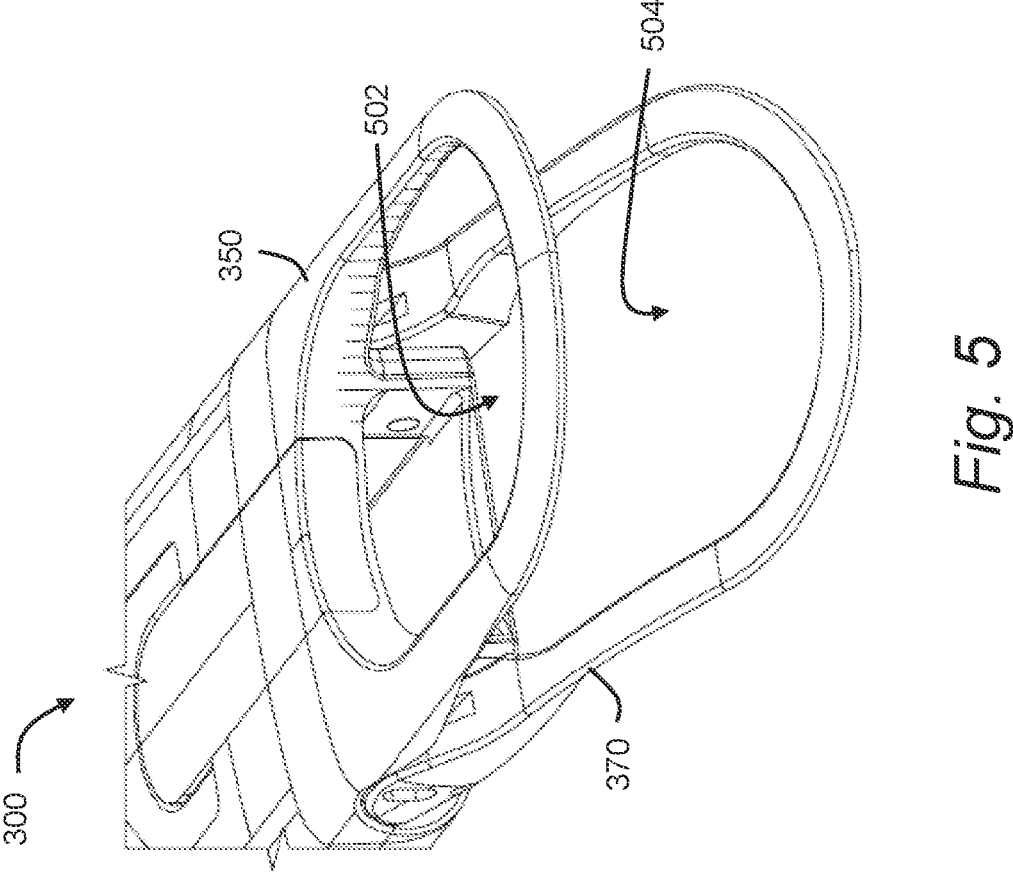
FIG. 5 is a perspective view of an endoscopic device with a movable jaw.

FIG. 5 is a perspective view of an endoscopic device with a movable jaw. The endoscopic device 500 may be any of the endoscopic devices described herein, except as specifically noted otherwise. In general, the endoscopic device 300 may include a first jaw 350 and a second jaw 370 extending from a distal end region of the endoscopic device 300. The first jaw 350 may define a first opening 502 passing through the first jaw 350 from the first interior surface 354 to the first exterior surface 356. The second jaw 370 may also or instead define a second opening 504 passing through the second jaw 370 from the second interior surface 384 to the second exterior surface 386. These openings 502, 504 can advantageously facilitate drainage of fluids from in and around the working volume 390 including native biological fluids at the surgical site, or saline or other fluids introduced to the working volume 390 during a surgical procedure. These openings also mitigate occlusions in the surgical field of view that might otherwise be caused by the jaws 350, 370, and permit better visibility, e.g., for a camera or other imaging device, throughout the working volume and surrounding tissue areas.

In one aspect, the first jaw 350 may form a wireframe structure about the first opening 502 where the shape of the first jaw 350 is defined around its perimeter by a thin structural member and the first opening 502 fills a majority of the surface area of the first exterior surface 356 (and the corresponding first interior surface 354) spanned by the wireframe structure of the first jaw 350. Similarly, the second jaw 370 may form a wireframe structure about the second opening 504 where the shape of the second jaw 370 is defined around its perimeter by a thin structural member and the second opening 504 fills a majority of the surface area of the second exterior surface 386 (and the corresponding second interior surface 384) spanned by the wireframe structure of the second jaw 370. More generally, large open spaces may usefully be employed in the first jaw 350 and the second jaw 370 to facilitate visibility and drainage during use of the endoscopic device 300. In another aspect, the first jaw 350 and/or the second jaw 370 may be formed of a mesh, perforated shell, or any other material or combination of materials that provides sufficient rigidity to displace tissue while promoting visibility and fluid drainage around a working volume created by the separated jaws 350, 370.

In another aspect, the leading edges of the first jaw 350 and the second jaw 370 may form u-shaped surfaces providing a rounded leading edge as the endoscopic device 600 advances along a surgical path.

Figure 6:
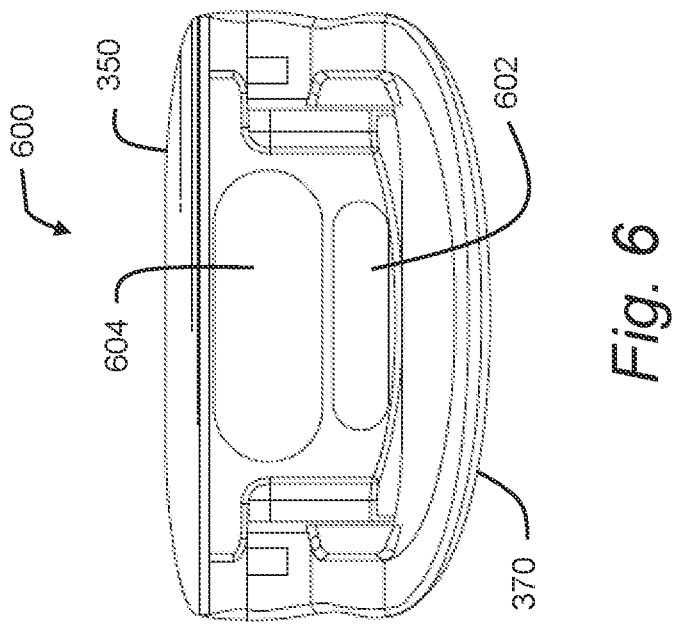
FIG. 6 is an end view of an endoscopic device.

FIG. 6 is an end view of an endoscopic device. The endoscopic device 600 may be any of the endoscopic devices described herein, except as specifically noted otherwise. In one aspect, the endoscopic device 600 may include a camera 602 and a working channel 604. The camera 602 may have a field of view directed toward the working volume between the first distal end of the first jaw 350 and the second distal end of the second jaw 370. The camera 602 may be electronically, optically, or otherwise coupled to a system for displaying the field of view at a remote location, e.g., on a display for a surgeon or other user of the device. The working channel 604 may provide a channel from a distal end to a proximal end of the endoscopic device 600 for the deployment of surgical tools, the deployment of surgical aids such as saline, the removal of tissue or other materials, and other physical access to and from a surgical site around and/or including the working volume. The working channel 604 may also be formed of an additional material or materials that provide additional mechanical support or stiffness along the length of the endoscopic device 600.

While the camera 602 is illustrated below the working channel 604 and adjacent to the second jaw 370, it will be understood that a variety of different positions may also or instead be employed. For example, the camera 602 may be positioned above the working channel 604 adjacent to the first jaw 370, or alongside the working channel 604 between the first jaw 350 and the second jaw 370. In addition, one or more illumination sources such as light emitting diodes may be included in the endoscopic device and positioned, e.g., adjacent to the camera 602, to illuminate a field of view for the camera 602. It will also be understood that, while a single working channel 604 is shown, any number of working channels may also or instead be included in the endoscopic device 300, and may vary according to the type of procedure, the diameter of the endoscopic device 300 and any other relevant factors. Thus, in one aspect, the endoscopic device 600 may include one or more supplemental instrument channels through the tube for deployment of one or more additional surgical tools to the distal end region of the tube.

Figure 7:
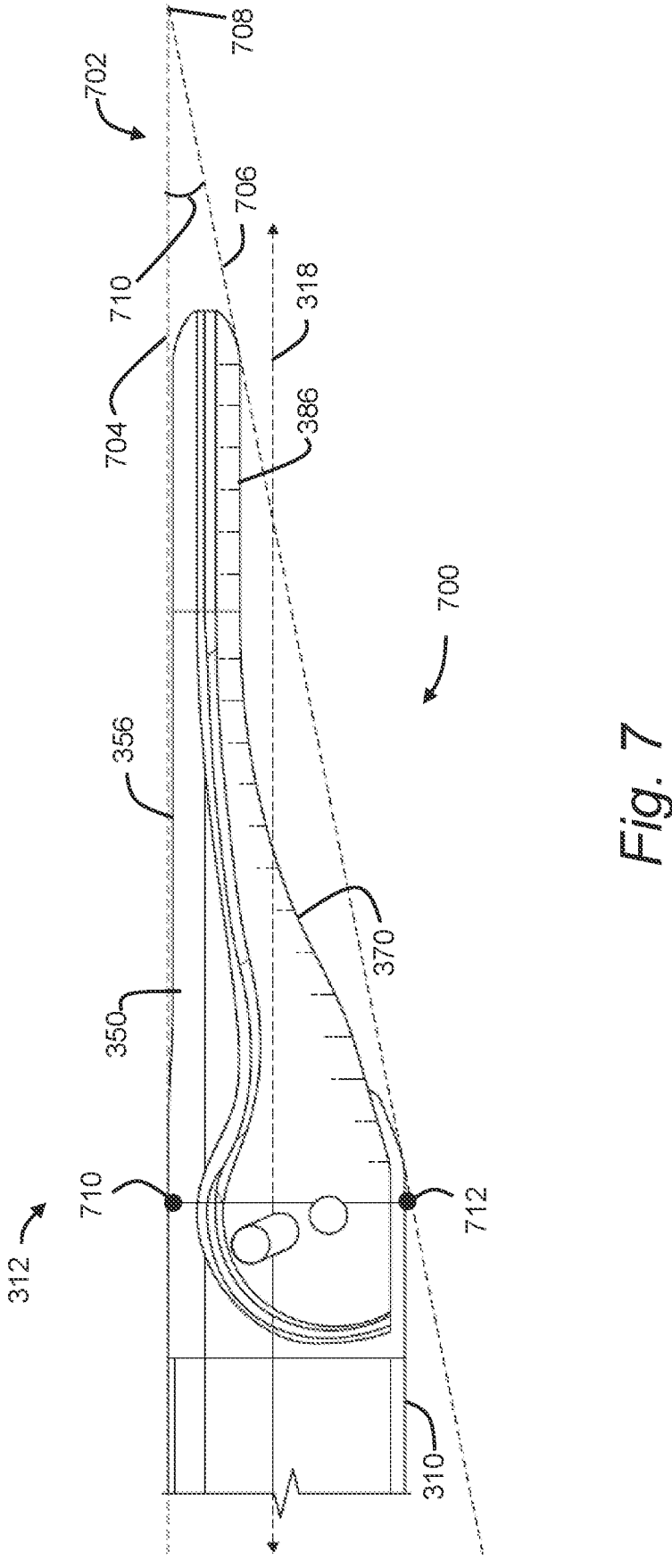
FIG. 7 shows a cross-section of an endoscopic device with a jaw in a closed position.

FIG. 7 shows a cross-section of an endoscopic device with a jaw in a closed position. The endoscopic device 700 may be any of the endoscopic devices described herein, except as specifically noted otherwise. In general, first jaw 350 and the second jaw 370 may have a closed position that is bounded by a wedge 702. This wedge shape, described in greater detail below, can advantageously facilitate advancement of the endoscopic device 700 along a space between two tissue layers to permit dissection of tissue coupling the adjacent layers.

In general, the wedge 702 described herein may be formed by two planar surfaces 704, 706 contacting two opposing sides of the tube 310 at the distal end region of the endoscopic device 700 and intersecting at a vertex 708 on the first side 304 of the plane passing through the central axis 318. It will be understood that the two planar surfaces 704, 706 are illustrated as lines that represent an intersection of these planar surfaces 704, 706 with the projection of FIG. 7, and that these planar surfaces 704, 706 may each be orthogonal to the surface of the illustration sheet. Stated differently, the two planar surfaces 704, 706 may extend normally from the plane of the cross-sectional view of FIG. 7. The two planar surfaces 704, 706 may be generally parallel to an axis of rotation of the pivot 352, and normal to the plane described above that divides the endoscopic device 700 into a first side 304 and a second side 306 along the central axis 318. Thus, in one aspect, the wedge 702 may contact a cross section of the first exterior surface 356 of the first jaw 350 and the second exterior surface 386 of the second jaw 370 in a second plane orthogonal to the plane through the central axis 318. At the vertex 708, the two planar surfaces 704, 706 may form an interior angle 710 of about five degrees to about thirty degrees, or an interior angle of about five to about sixty degrees, or about ten to thirty degrees, or about ten to about sixty degrees, or any angle or range of angles between any of these example ranges.

In another aspect, the wedge 702 may be an asymmetrical wedge with the vertex 708 away from the central axis 318. For example, a first planar surface 704 of the wedge 702 may extend from and be parallel with an exterior side of the tube 310 where the tube 310 joins the first jaw 350. In another aspect, the wedge 702 may include a first planar surface 704 substantially parallel to the central axis 318 and aligned with a point 710 on an exterior surface of the distal end region 312 of the tube 310, and a second planar surface 706 intersecting a radially opposing point 712 on the exterior surface of the distal end region 312 of the tube, where, as generally noted above, the two planar surfaces 704, 706 envelope the two jaws 350, 370 in the closed position. More generally, an asymmetrical wedge may be formed with the vertex 708 of the wedge 702 radially closer to an exterior of the tube than the central axis 318 of the tube, e.g., when looking along the central axis 318, or within a projection along the central axis 318.

It will be appreciated that, while the points of contact 710, 712 between the wedge 702 and the tube 310 are illustrated as being at similar axial positions lengthwise along the central axis 318, this is not strictly geometrically required. The distal end region 312 of the endoscopic device 700 may take many generally wedge-like shapes, and the wedge 702 may more generally contact any point or points along a convex hull of the distal end region 312 such that the wedge 702 contacts at least one point on each side of the plan passing through the central axis 318, and the wedge 702 wholly encompasses (inclusively, e.g., including points of contact) the distal end region 312 when the endoscopic device 700 is in a closed position.

In general, this wedge shape, and in particular, the asymmetrical wedge shape, advantageously permits the endoscopic device 700 to be advanced between two layers of tissue within a surgical site, with the first jaw 350 remaining in contact with one of the tissue layers in order to preferentially follow that tissue layer while advancing. The ends of the first jaw 350 and the second jaw 370 may converge near the vertex 708 of the wedge 702 to steer the endoscopic device 700 between the two layers and urge the tissue layers apart as the endoscopic device 700 advances.

Figure 8:
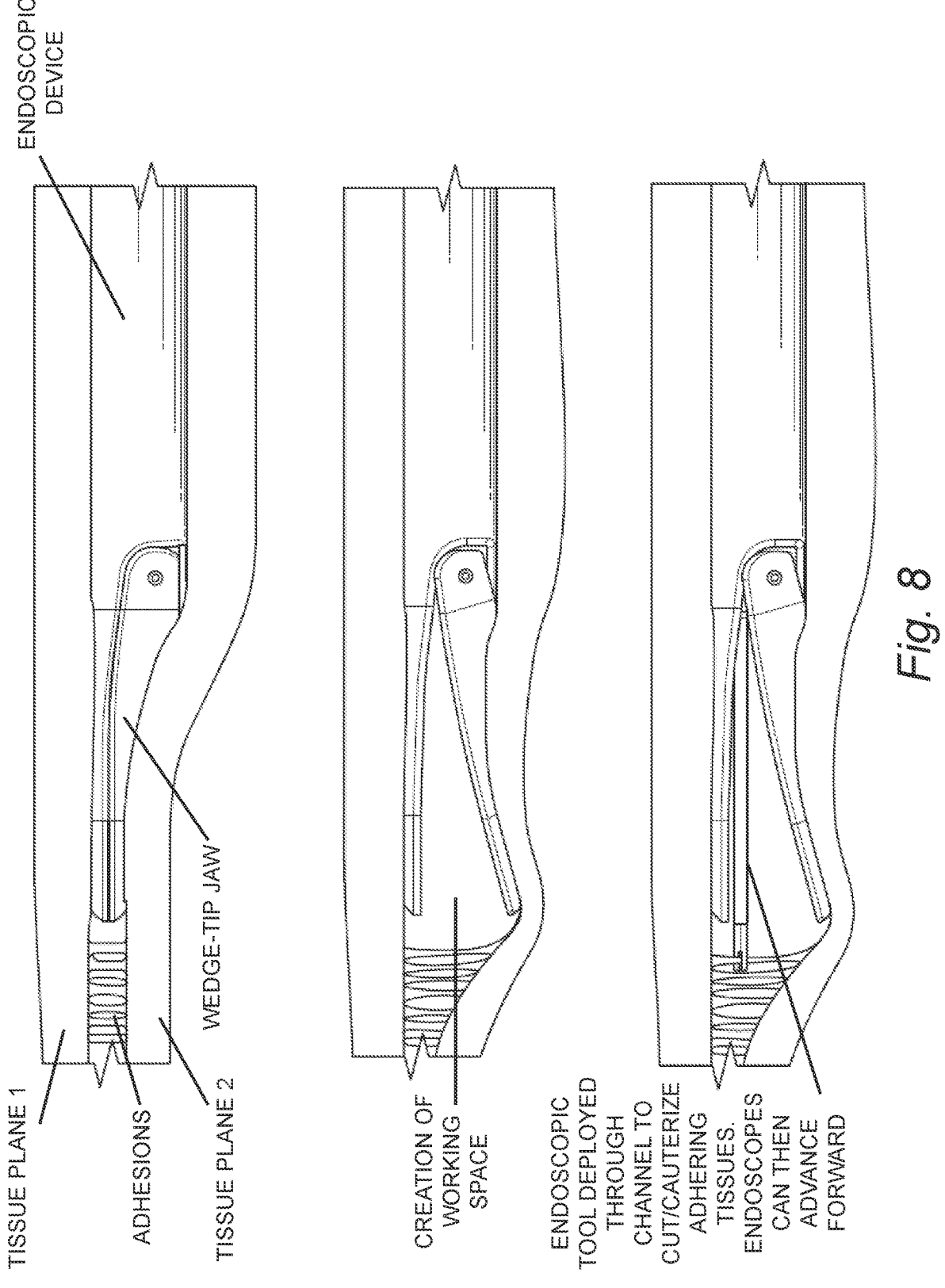
FIG. 8 illustrates an endoscopic device used in a surgical procedure.

FIG. 8 illustrates an endoscopic device used in a surgical procedure. In general, the tip or vertex of the jaw is advanced toward adhesions or other connective structures between two adjacent tissue planes or layers. When inserted into this space, the jaws may be opened (e.g., by actuating a handle of the endoscopic device) to create a working volume between the two tissue layers. An endoscopic tool such as a cutting tool may then be advanced through a working channel of the endoscopic device to cut, cauterize, or otherwise dissect or remove the connective structures, thus clearing a path for the endoscopic device to be further advanced in a direction toward a surgical site where a surgery is to be performed.

In one aspect, the surgery may include a procedure such as dissecting retrosternal adhesions prior to a resternotomy. In general, adhesions may form between the heart and the sternum after a sternotomy, increasing the time and risk for subsequent sternotomies. In this context, a minimally invasive tool for interlayer tissue dissection can facilitate subsequent procedures by providing a device targeted at dissection of adhesions of the conjoined tissue without requiring open surgery. This principle may also or instead be usefully employed in a range of minimally invasive procedures involving interlayer dissection such as a minimally invasive coronary artery bypass surgery, a minimally invasive thymectomy, or other surgical applications such as mediastinoscopy, endoscopic breast surgery, or extraperitoneal ventral hernia repairs.

Figure 9:
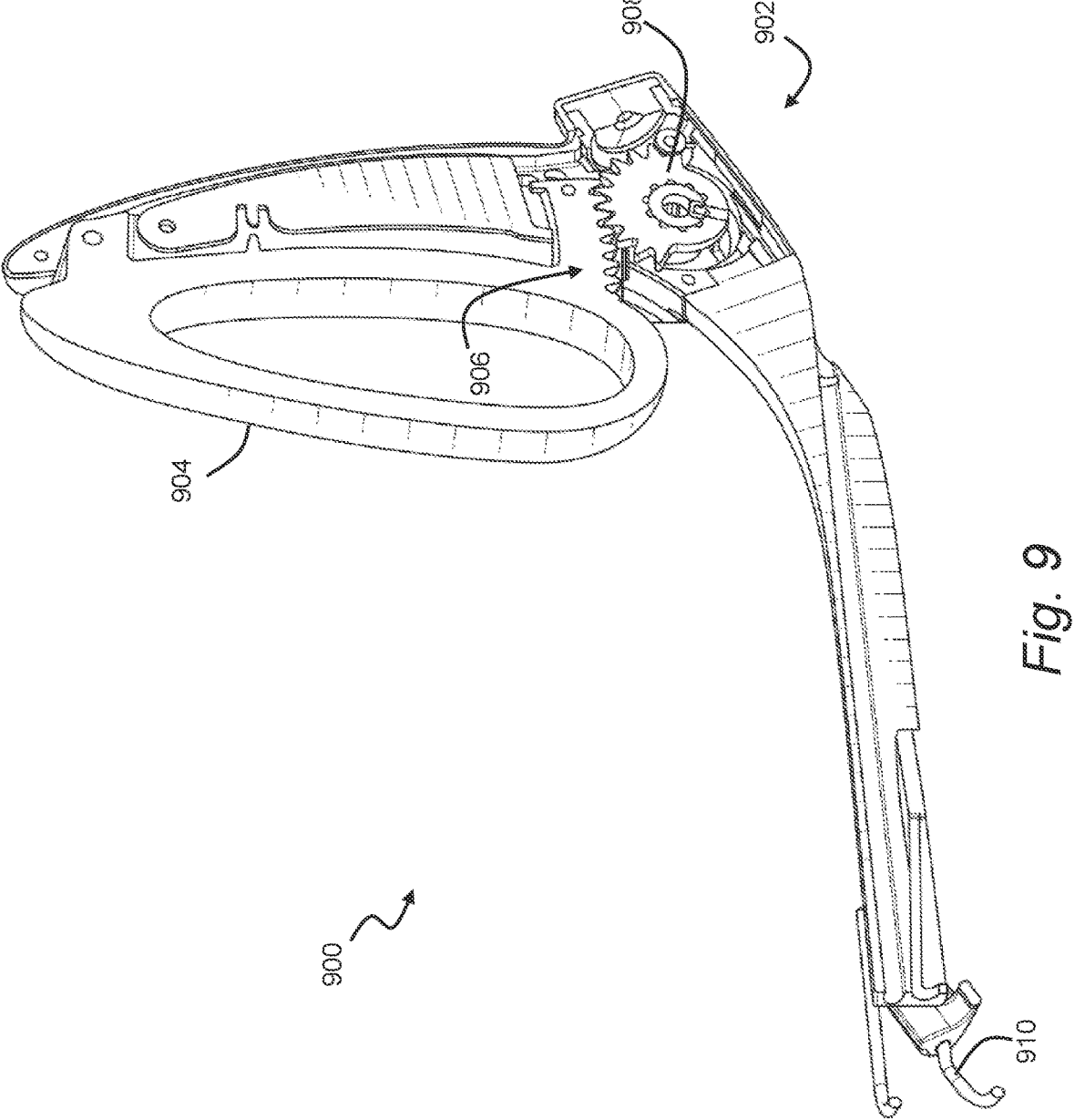
FIG. 9 shows a jaw transmission for an endoscopic device.

FIG. 9 shows a jaw transmission for an endoscopic device. In general, the endoscopic device 900 may be any of the endoscopic devices described herein, except as specifically otherwise noted. In one aspect, the endoscopic device 900 may include a gear and capstan assembly 902 including a handle 904 with a gear 906 that couples the handle 904 to a capstan 908, which in turn drives a linkage to a moving jaw 910. This arrangement provides an additional mechanism— the gearing ratio—for controlling the degree of mechanical advantage provided in the transmission of force from the handle to the moving jaw 910. Other techniques such as a cable/pulley system, multiple gears, hydraulic systems, or the like may also or instead be employed to transmit manual force by a user to actuate the moving jaw 910 of the endoscopic device 900. It will also be appreciated that, while the endoscopic device 900 of FIG. 9 is illustrated with a rigid housing, the exterior of the endoscopic body may also or instead include a flexible length as necessary and/or helpful for use in different surgical contexts, e.g., for adaptation to different physiological geometries and surgical procedures.

Figures 10, 11, 12:
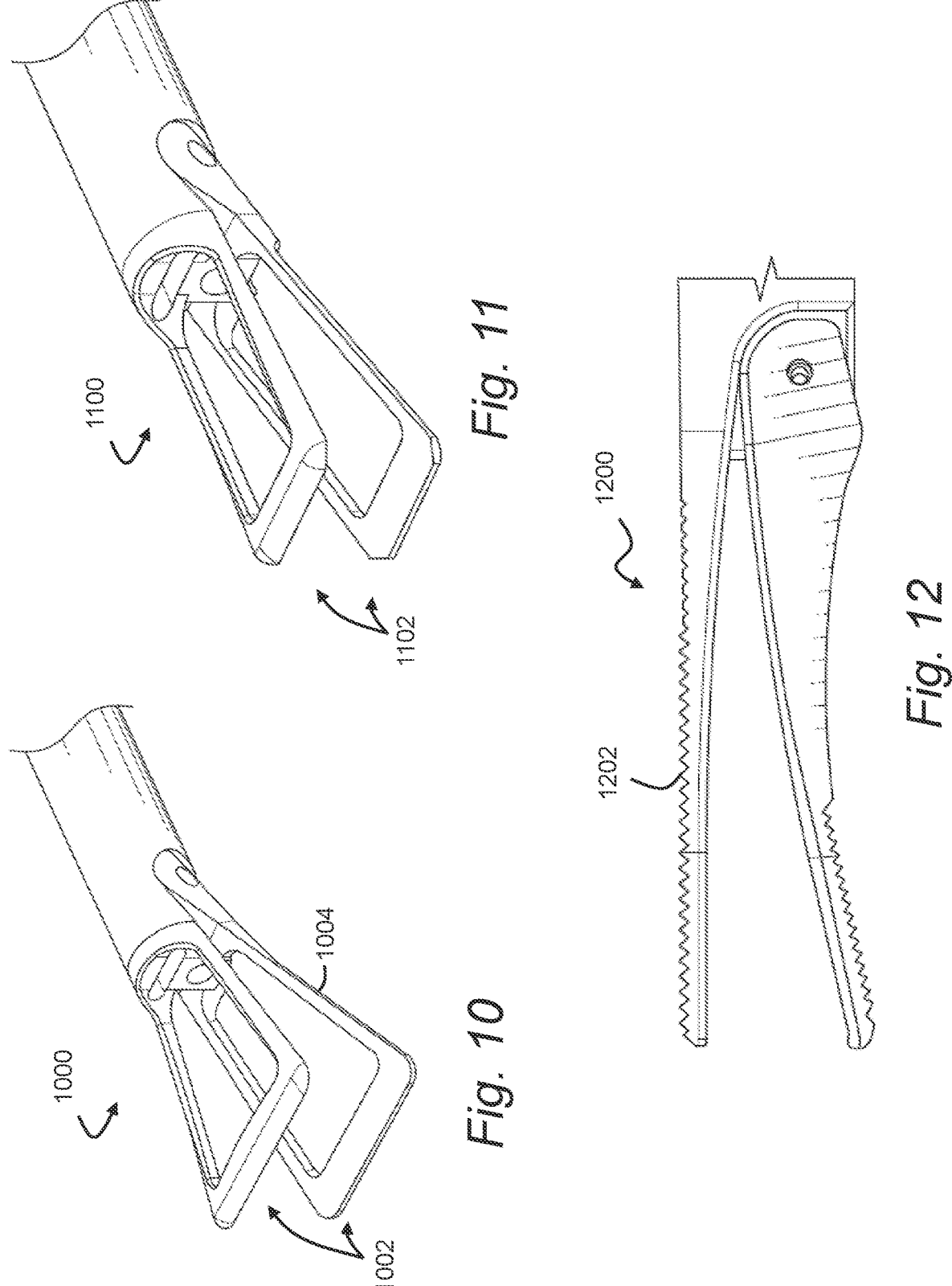
FIG. 10 shows an endoscopic device.
FIG. 11 shows an endoscopic device.
FIG. 12 shows an endoscopic device.

FIG. 10 shows an endoscopic device 1000. The endoscopic device 1000 may be any of the endoscopic devices described herein, except as specifically noted otherwise. In an embodiment, the ends 1002 of the jaws 1004 of the endoscopic device 1000 may flair outward from the envelope of the tube and provide a straight edge at the distal end orthogonal to the direction of movement. This general shape, where geometrically suitable to a surgical site, can increase the effective width of the working volume provided by the separating jaws, thus affording a greater range of movement for a cutting tool or other endoscopic tool deployed through a working channel of the device 1000.

FIG. 11 shows an endoscopic device 1100. The endoscopic device 1100 may be any of the endoscopic devices described herein, except as specifically noted otherwise. In an embodiment, the leading edge 1102 or distal end of the jaws may provide a straight edge orthogonal to the direction of movement. It will also be noted that the tips of the first jaw and second jaw may meet closer to a center access of the endoscopic device 1100, thus driving the wedge more centrally between two tissue layers, rather than preferentially following one of the layers with the surface of the fixed jaw, e.g., when using one of the asymmetrical wedges described above. Although the two jaws meet in a location closer to the central axis, the pivot may still preferably be placed on a side of the central axis opposing the first (stationary) jaw, in order to facilitate a motion that creates a working volume aligned to the center axis for deployment of surgical tools and the like.

It will also be understood that the endoscopic device 1100 may usefully have a generally circular cross-section along its length. This shape can facilitate deployment through a conventional, minimally invasive trocar while permitting axial rotation as necessary or helpful during a surgical procedure. In another aspect, the cross-section may be flattened, e.g., to form an oval, rectangle (e.g., with rounded edges, as depicted in FIG. 6), or the like, to resist axial rotation of the endoscopic device during a procedure.

FIG. 12 shows an endoscopic device 1200. The endoscopic device 1200 may be any of the endoscopic devices described herein, except as specifically noted otherwise. In one aspect, the endoscopic device 1200 may include serrations 1202 on at least one of the first exterior surface (of the first, stationary jaw) and the second exterior surface (of the second, moving jaw). These serrations may form teeth or the like oriented to resist a retreat of the first jaw and the second jaw along a forward surgical path of the endoscopic device 1200. Thus, as distinguished from the smooth finish illustrated in the preceding drawings, the endoscopic device 1200 may include lateral serrations with ridges running perpendicular to the central axis of the device (e.g., perpendicular to a direction of motion of the endoscopic device 1200), cross serrations such as a cross-hatched pattern of serrations, or any other pattern or combination of patterns suitable for engaging the jaw(s) with surrounding tissue to retain position and minimize unintended movement of the endoscopic device 1200 forward and/or backward along a path toward a surgical site during a procedure.

Numerous variations and adaptations are possible. For example, the endoscopic device may be incorporated into a surgical robotic system, e.g., for navigating the endoscopic device to a surgical site, or for activating the components of the endoscopic device remotely such as the jaw, a cutting device, a camera, and so forth.

It will be appreciated that the methods and systems described above are set forth by way of example and not of limitation. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context. Thus, while particular embodiments have been shown and described, it will be apparent to those skilled in the art that various changes and modifications in form and details may be made therein without departing from the spirit and scope of this disclosure and are intended to form a part of the invention as defined by the following claims.

The invention claimed is:

1. An endoscopic device comprising:
a tube having a distal end region, a proximal end region, and a central axis passing through the distal end region, the tube defining a channel from the proximal end region to the distal end region;
a first jaw extending from the distal end region of the endoscopic device on a first side of a plane through the central axis, the first jaw having a first interior surface oriented toward the central axis and a first exterior surface oriented away from the central axis, the first jaw defining a first opening passing through the first jaw from the first interior surface to the first exterior surface;
a second jaw extending from the distal end region of the endoscopic device, the second jaw pivotally coupled to the distal end region by a pivot on a second side of the plane opposing the first side, the second jaw including a second interior surface facing the first jaw and a second exterior surface facing away from the first jaw, the second jaw defining a second opening passing through the second jaw from the second interior surface to the second exterior surface, the second jaw having a closed position in which the first jaw and the second jaw are bounded by a wedge formed by two planar surfaces intersecting at a vertex on the first side of the plane, and the second jaw movable about the pivot to an open position wherein a second distal end of the second jaw moves across the central axis to the second side of the plane to create a working volume about the plane between a first distal end of the first jaw and the second distal end of the second jaw;
a cutting tool configured to advance through a working channel in the tube and into the working volume to dissect connective structures and create a path for advancing the endoscopic device toward a surgical site; and
an actuator operable to move the second jaw between the closed position and the open position.

2. The endoscopic device of claim 1 further comprising a camera having a field of view directed toward the working volume between the first distal end of the first jaw and the second distal end of the second jaw.

3. The endoscopic device of claim 1 wherein the wedge contacts a cross section of the first exterior surface of the first jaw and the second exterior surface of the second jaw in a second plane orthogonal to the plane through the central axis, the wedge forming an angle of about five degrees to about thirty degrees.

4. The endoscopic device of claim 1 wherein the wedge forms an envelope about the first exterior surface of the first jaw and the second exterior surface of the second jaw having an angle of about five to about sixty degrees.

5. The endoscopic device of claim 1 wherein the wedge is an asymmetrical wedge.

6. The endoscopic device of claim 1 wherein a first planar surface of the wedge extends from and is parallel to an exterior side of the tube.

7. The endoscopic device of claim 1 wherein the vertex of the wedge is radially closer to an exterior of the tube than the central axis of the tube.

8. The endoscopic device of claim 1 wherein the wedge includes a first planar surface substantially parallel to the central axis and aligned with a point on an exterior surface of the distal end region of the tube, and a second planar surface intersecting a radially opposing point on the exterior surface of the distal end region of the tube.

9. The endoscopic device of claim 8 wherein the first planar surface and the second planar surface form an interior angle of the wedge of about ten to thirty degrees.

10. The endoscopic device of claim 1 wherein the first exterior surface of the first jaw extends from and is aligned with an exterior surface of the distal end region of the tube.

11. The endoscopic device of claim 1 wherein the first jaw is a wireframe structure formed about the first opening such that the first opening spans a majority of a surface area of the first exterior surface.

12. The endoscopic device of claim 1 wherein the second jaw is a wireframe structure formed about the second opening such that the second opening spans a majority of a surface area of the second exterior surface.

13. The endoscopic device of claim 1 further comprising a handle on the proximal end region of the tube, the handle coupled to the second jaw through a jaw transmission configured to rotate the second jaw about the pivot in response to a movement of the handle.

14. The endoscopic device of claim 13 further comprising a sheet metal linkage for communicating a force from the handle to the distal end region for rotation of the second jaw about the pivot.

15. The endoscopic device of claim 13 further comprising a gear and capstan for communicating a force from the handle to the distal end region for rotation of the second jaw about the pivot.

16. The endoscopic device of claim 1 further comprising serrations on the first exterior surface of the first jaw oriented to resist a retreat of the endoscopic device along a forward surgical path.

17. The endoscopic device of claim 1 further comprising serrations on the second exterior surface of the second jaw oriented to resist a retreat of the endoscopic device along a forward surgical path.

18. An endoscopic device comprising:
a tube including a distal end region, a proximal end region, and a central axis passing through the distal end region, the tube defining a channel from the proximal end region to the distal end region;

a first jaw fixed to and extending from the distal end region of the endoscopic device on a first side of a plane through the central axis, the first jaw having a first interior surface oriented toward the central axis and a first exterior surface oriented away from the central axis;

a second jaw extending from the distal end region of the endoscopic device, the second jaw pivotally coupled to the distal end region by a pivot on a second side of the plane opposing the first side, the first jaw and the second jaw having a closed position bounded by a wedge formed by two planar surfaces intersecting at a vertex on the first side of the plane, and the second jaw movable about the pivot to an open position wherein a second distal end of the second jaw moves across the central axis to the second side of the plane to create a working volume about the plane between a first distal end of the first jaw and the second distal end of the second jaw, wherein the two planar surfaces forming the wedge contact two opposing sides of the tube at the distal end region of the tube and envelope a convex hull of the first jaw and the second jaw in an asymmetric wedge parallel to a side of the tube on a first wedge side and contacting a distal end of the second jaw on a second wedge side, the first wedge side and the second wedge side forming the vertex radially closer to an exterior of the tube than the central axis and forming an interior angle not greater than thirty degrees; and an actuator operable to move the second jaw between the closed position and the open position.

19. The endoscopic device of claim 18 wherein the first jaw defines a first opening passing through the first jaw from the first interior surface to the first exterior surface.

20. The endoscopic device of claim 18 wherein the second jaw includes a second interior surface facing the first jaw and a second exterior surface facing away from the first jaw, the second jaw defining a second opening passing through the second jaw from the second interior surface to the second exterior surface.

* * * * *